(12) United States Patent
Chen et al.

(10) Patent No.: US 12,083,355 B1
(45) Date of Patent: Sep. 10, 2024

(54) PREPARATION OF PHOTODYNAMIC THERAPY TABLET AND METHOD FOR CONSTRUCTION AND APPLICATION OF ANTI-TUMOR MODEL FOR ENHANCED CANCER TREATMENT

(71) Applicant: Sichuan Cancer Hospital, Chengdu (CN)

(72) Inventors: Meihua Chen, Chengdu (CN); Pingjin Zou, Chengdu (CN); Xinyu Xue, Chengdu (CN); Jinyi Lang, Chengdu (CN); Lili Xing, Chengdu (CN); Rui Lin, Chengdu (CN)

(73) Assignee: Sichuan Cancer Hospital, Chengdu (CN)

( * ) Notice: Subject to any disclaimer, the term of this patent is extended or adjusted under 35 U.S.C. 154(b) by 0 days.

(21) Appl. No.: 18/400,131

(22) Filed: Dec. 29, 2023

(30) Foreign Application Priority Data

Jul. 12, 2023 (CN) .......................... 202310850855.2

(51) Int. Cl.
  *A61N 5/06* (2006.01)
  *A61K 41/00* (2020.01)
  (Continued)

(52) U.S. Cl.
  CPC .......... *A61N 5/062* (2013.01); *A61K 41/0071* (2013.01); *C12N 5/0693* (2013.01);
  (Continued)

(58) Field of Classification Search
  CPC .................. A61N 5/0601; A61N 5/062; A61N 2005/0632; A61N 2005/0651;
  (Continued)

(56) References Cited

U.S. PATENT DOCUMENTS 6,273,904 B1 * 8/2001 Chen ...................... A61N 5/062
  606/14
8,886,334 B2 * 11/2014 Ghaffari ................. A61B 5/145
  607/115
(Continued)

FOREIGN PATENT DOCUMENTS

CN  104767291 A   7/2015
CN  111741794 A  10/2020
(Continued)

OTHER PUBLICATIONS

WO2017044701A1 (Year: 2017).*

*Primary Examiner* — Ahmed M Farah
(74) *Attorney, Agent, or Firm* — Andrew D. Fortney; Central California IP Group, P.C.

(57) ABSTRACT

A photodynamic therapy tablet and corresponding preparation method, as well as a construction method and system specifically designed for anti-tumor models, are disclosed. The tablet includes a wireless power supply unit, a circuit unit, micrometer-level LED array, and a flexible transparent biocompatible encapsulation. It can be surgically implanted in close proximity to tumor cells within the human body, enabling precise irradiation of the targeted tumor cells. By harnessing light of a specific wavelength, the tablet facilitates the generation of lipid peroxides, which, in conjunction with a ferroptosis inducer, effectively triggers ferroptotic cell death in tumor cells. The ultrasound wireless self-powering photodynamic therapy tablet is utilized for the treatment of tumor cells through photodynamic therapy (PDT). By combining the ferroptosis inducer with PDT, the present invention effectively addresses the issue of limited efficacy observed when using the ferroptosis inducer alone.

6 Claims, 5 Drawing Sheets

(51) Int. Cl.
  *C12N 5/09*     (2010.01)
  *C12N 13/00*    (2006.01)
  *G01N 33/50*    (2006.01)
  *H05B 45/30*    (2020.01)

(52) U.S. Cl.
  CPC ......... *C12N 13/00* (2013.01); *G01N 33/5091* (2013.01); *H05B 45/30* (2020.01); *A61N 2005/0652* (2013.01)

(58) Field of Classification Search
  CPC ............ A61N 2005/0652; H05B 45/30; H05B 45/34; H05B 45/357; H05B 45/37; H05B 45/3725; H05B 45/39; H05B 45/40
  USPC .......................................................... 607/88
  See application file for complete search history.

(56) References Cited

U.S. PATENT DOCUMENTS

| | | | |
|---|---|---|---|
| 10,130,802 B2 * | 11/2018 | Chae ....................... | A61N 5/062 |
| 11,154,201 B2 * | 10/2021 | Rogers ................. | A61B 5/6868 |
| 11,389,665 B2 * | 7/2022 | Sa .......................... | A61N 5/062 |
| 2020/0406052 A1 * | 12/2020 | Yin ....................... | A61N 5/0603 |
| 2021/0060350 A1 | 3/2021 | Ho et al. | |
| 2023/0147752 A1 * | 5/2023 | Rezaie ................. | A61N 5/0624 |
| | | | 607/94 |

FOREIGN PATENT DOCUMENTS

| | | | | |
|---|---|---|---|---|
| CN | 114656398 A | 6/2022 | | |
| CN | 114949623 A | 8/2022 | | |
| WO | WO 2017/044701 A * | 3/2017 | ............. | A61K 47/40 |

* cited by examiner

PREPARATION OF PHOTODYNAMIC THERAPY TABLET AND METHOD FOR CONSTRUCTION AND APPLICATION OF ANTI-TUMOR MODEL FOR ENHANCED CANCER TREATMENT

RELATED APPLICATION(S)

This application claims the benefit of Chinese Application No. 202310850855.2, filed on Jul. 12, 2023 in the National Intellectual Property Administration, PRC (CNIPA), incorporated herein by reference.

TECHNICAL FIELD

This invention belongs to the field of cancer physical therapy technology, particularly relating to a photodynamic therapy tablet and its preparation method, as well as a construction method and system for an anti-tumor model based on the photodynamic therapy tablet.

BACKGROUND

Despite significant breakthroughs in diagnosis and treatment, cancer remains a leading cause of human mortality. Current mainstays of cancer treatment include surgery, chemotherapy, radiation therapy, targeted therapy, and immunotherapy. However, innate and acquired resistance exhibited by cancer patients poses a significant obstacle to effective treatment.

Ferroptosis, a newly recognized form of programmed cell death (PCD) triggered by lipid peroxidation, offers a novel avenue for therapeutic intervention. Ferroptosis can be induced through both exogenous and endogenous pathways. The exogenous pathway involves inhibition of cellular membrane transport proteins, while the endogenous pathway is characterized by blocking intracellular antioxidant enzyme activation. Cancer cells that exhibit resistance to apoptosis, whether due to their highly stromal state or as a result of chemotherapy, display heightened sensitivity to ferroptosis. Inducing ferroptosis in tumor cells selectively using ferroptosis inducers (FINs) can restore their sensitivity to conventional therapies and represents a promising approach for cancer treatment.

Currently known ferroptosis inducers include small molecule drugs in preclinical studies such as erastin, RSL3, and $FINO_2$, as well as clinically used drugs like azo-sulfonamide pyridine, cisplatin, statins, and artemisinin, among others. However, these small molecule drugs suffer from drawbacks such as significant side effects, lack of targeting specificity, and poor solubility, which severely impact their anti-tumor efficacy. Additionally, improved drug formulations utilizing nanosynthesis techniques, such as those involving exosomes, suffer from limitations such as low production yield, production instability, and high costs.

To enhance the anti-tumor effects of ferroptosis inducers, combination therapy with other treatment modalities is often required. However, co-administration with traditional radiotherapy and chemotherapy can lead to damage to normal tissues and organs, poor targeting specificity, and the emergence of resistance mechanisms, thereby increasing the risk of severe toxic side effects and compromising the anti-tumor efficacy.

SUMMARY

The present invention relates to a tablet for photodynamic therapy (PDT) and its preparation method. Additionally, it encompasses a method and system for constructing an anti-tumor model. This invention effectively addresses the limitations observed in current technologies by leveraging the reactive oxygen species (ROS) generated during PDT to stimulate the production of lipid peroxides in tumor cells. This induction subsequently triggers ferroptosis, thereby enhancing the effectiveness of existing ferroptosis inducers. The primary objective of this invention is to overcome the issue of insufficient anti-tumor efficacy when solely relying on ferroptosis inducers.

To accomplish the aforementioned objectives of the invention, the technical solution employed is as follows:

The present invention introduces a wireless self-powered photodynamic tablet that comprises several key components. These include a wireless power supply unit, a circuit unit that is electrically connected (e.g., to the wireless power supply unit), a micrometer-scale LED array that is connected to the circuit unit, and a flexible transparent biocompatible encapsulation that encloses the wireless power supply unit, circuit unit, and micrometer-scale LED array.

The wireless power supply unit is configured to receive ultrasound energy and convert it into electrical energy.

The circuit unit rectifies the electrical energy generated by the wireless power supply unit into direct current and ensures stable transmission (e.g., of electrical current) to the micrometer-scale LED array.

The micrometer-scale LED array, in turn, receive the direct current and emits light of a predetermined wavelength. This emitted light facilitates the production of lipid peroxides in tumor cells, working in conjunction with ferroptosis inducers to induce iron-dependent cell death specifically in tumor cells.

The invention offers several significant beneficial effects, which are outlined as follows:

(1). The utilization of the wireless power supply unit allows for the conversion of ultrasound energy into electrical energy, while the circuit unit further converts it into stable direct current. This provides the foundation for the micrometer-scale LED array to emit light of a specific wavelength during PDT. By irradiating a photosensitizer at the tumor site with the appropriate wavelength of light, the production of lipid peroxides in tumor cells is promoted under aerobic conditions. The combination of lipid peroxides and ferroptosis inducers induces iron-dependent cell death specifically in tumor cells, thereby restoring their sensitivity to conventional treatments. This combination approach not only improves targeting and overcomes drug resistance, but also reduces toxic side effects, leading to a significant reduction in damage to normal tissues and organs. The ferroptosis inducers, upon inducing iron-dependent cell death, result in the accumulation of ferrous ions within the cells. This accumulation, in turn, triggers the generation of oxygen through the Fenton reaction. Consequently, the tumor's hypoxic microenvironment is improved, and an adequate oxygen supply is provided for PDT. This synergistic effect enhances the overall effectiveness in combating tumors.

(2). The incorporation of flexible transparent biocompatible encapsulation significantly enhances the biocompatibility of the tablet, effectively mitigating potential harm such as thermal effects on normal tissues. Additionally, the transparency of the encapsulation material facilitates efficient light irradiation during PDT by the micrometer-scale LED array.

Furthermore, the use of a square, plate-shaped piezoelectric ceramic comprising lead zirconate titanate in the wireless power supply unit further enhances the beneficial effect of the invention. This design leverages small deformations on the surface of the piezoelectric ceramic, which may be caused by the reception of ultrasound, to convert mechanical energy into electrical energy through the piezoelectric effect. The square, plate-shaped structure ensures optimal reception by the wireless power supply unit.

In terms of dimensions, the wireless self-powered photodynamic tablet has a length of 8 mm, a width of 5 mm, and a height of 3 mm, with a weight of 0.44 g.

The square, plate-shaped piezoelectric ceramic measures 4 mm in length and width, with a height of 1 mm.

The LEDs within the micrometer-scale LED array have a length of 1 mm, and a width and height of 0.5 mm.

These dimensions allow for easy implantation of the tablet into the body with minimal incision size. They also enable precise targeting of tumor cells for effective PDT. Furthermore, these dimensions ensure sufficient ultrasound reception and adequate illumination by the micrometer-scale LED array, preventing insufficient PDT treatment effects.

The wireless self-powered photodynamic tablet, in combination with ferroptosis inducers, offers a synergistic approach for anti-tumor therapy, further enhancing its efficacy.

The circuit unit of the invention comprises a rectifier bridge and a voltage-stabilizing capacitor, which are interconnected to facilitate the transmission of electrical energy to the micrometer-scale LED array. The rectifier bridge may include four Schottky barrier diodes: the first, second, third, and fourth diodes.

The positive terminal of the first Schottky barrier diode serves as the positive terminal of the rectifier bridge. It is connected to the positive terminals of the third Schottky barrier diode, the voltage-stabilizing capacitor, and the negative terminal of the micrometer-scale LED array. The negative terminal of the first Schottky barrier diode is connected to the positive terminal of the second Schottky barrier diode and one end of the wireless power supply unit. The negative terminal of the second Schottky barrier diode serves as the negative terminal of the rectifier bridge. It is connected to the negative terminals of the fourth Schottky barrier diode, the other end of the voltage-stabilizing capacitor, and the positive terminal of the micrometer-scale LED array. The negative terminals of the third and fourth Schottky barrier diodes are connected to the positive terminal of the fourth Schottky barrier diode and the other end of the wireless power supply unit, respectively. The rectifier bridge plays a crucial role in converting the alternating current generated by the wireless power supply unit into direct current, which is necessary for the operation of the micrometer-scale LED array. The voltage-stabilizing capacitor serves to stabilize the transmission of the direct current to the micrometer-scale LED array, ensuring a consistent and reliable power supply for optimal performance.

The described additional solution offers the following advantageous effects: It utilizes a rectifier bridge and a voltage-stabilizing capacitor to convert the electrical energy generated by the wireless power supply unit into stable direct current. This converted current powers the micrometer-scale LED array during PDT. The Schottky barrier diodes employed in the rectifier bridge exhibit rapid reverse recovery speeds in the order of nanoseconds, low power consumption, and a capacity to handle high currents. These diodes demonstrate reduced susceptibility to reverse leakage or heating, thus minimizing the risk of burning in high-frequency applications.

The present invention encompasses a method for preparing a wireless self-powered photodynamic tablet to attain the aforementioned technical effects. The preparation method involves the following steps:

Pre-clean the wireless power supply unit using ethanol and deionized water, and subsequently drying it in an oven.

Solder the wireless power supply unit and circuit unit onto one side of the circuit board, ensuring a secure electrical connection between them.

Solder the micrometer-scale LED array onto another side of the circuit board, ensuring a reliable electrical connection between the circuit unit and the LED array.

Encapsulate the soldered wireless power supply unit, circuit unit, and micrometer-scale LED array with a flexible, transparent, and biocompatible material. Allow the encapsulation to dry thoroughly.

The present invention offers several beneficial effects. Firstly, it provides a preparation method for a wireless self-powered photodynamic tablet. By strategically placing the wireless power supply unit and circuit unit on one side of the circuit board, and the micrometer-scale LED array on the other side, the tablet's size is significantly reduced. This arrangement ensures that one side of the tablet receives ultrasound waves, while the other side emits light of a specific wavelength for PDT in real time.

To attain the aforementioned technical effects, the present invention introduces a treatment system centered around the wireless self-powered photodynamic tablet. This comprehensive system comprises the wireless self-powered photodynamic tablet itself and an ultrasound probe specifically designed to emit ultrasound waves to the tablet.

The present invention offers several beneficial effects. One notable effect is achieved by utilizing the ultrasound probe to emit ultrasound waves to the wireless self-powered photodynamic tablet. This process serves as the foundation for the tablet to acquire electrical energy, enabling simultaneous wireless power supply and treatment control. As a result, this facilitates deep treatment and enhances the overall efficacy of the therapeutic process.

To accomplish the aforementioned technical effects, the present invention additionally presents a system for constructing an anti-tumor model. This system incorporates a base equipped with a cell culture device, and an ultrasound probe that is externally connected to the base for emitting ultrasound waves. Moreover, the system integrates the wireless self-powered photodynamic tablet, which plays a crucial role in emitting light of a predetermined wavelength to the cell culture device. This light exposure promotes the production of lipid peroxides in tumor cells. Furthermore, the wireless self-powered photodynamic tablet is combined with a ferroptosis inducer, which effectively induces iron-dependent cell death in tumor cells.

The present invention yields the following technical effects: It establishes an anti-tumor model that utilizes the wireless self-powered tablet driven by ultrasound to emit light of a specific wavelength for PDT. This innovative model not only enables targeted treatment, but also forms the basis for combining PDT with a ferroptosis inducer, thereby enhancing the effectiveness of anti-tumor treatment.

Additionally, a medical ultrasound gel layer is introduced between the cell culture device and an upper surface of the base.

The introduction of this additional solution offers a beneficial effect. By placing a medical ultrasound gel layer between the cell culture device and the upper surface of the base, it effectively eliminates excess air space and enhances the utilization efficiency of ultrasound energy.

Furthermore, the cell culture device is constructed using a transparent porous plate, and the wireless self-powered photodynamic tablet is positioned in the medical ultrasound gel layer.

This additional solution offers a beneficial effect. By utilizing a transparent porous plate made of transparent material for the cell culture device, it becomes feasible to conduct comparative anti-tumor research while minimizing errors attributable to environmental factors. The transparent material is highly responsive to photodynamic therapy (PDT) and facilitates the successful emission of light with a specific wavelength by the tablet, enabling effective deep treatment.

To achieve the aforementioned technical effects, the present invention provides a method for constructing an anti-tumor model using the wireless self-powered photodynamic tablet. This method is implemented based on the system for constructing an anti-tumor model and involves the following steps:

Inoculate a certain number of tumor cells into the holes (e.g., spaces, wells, depressions, etc.) of the cell culture device and allow them to adhere and grow.

Remove the culture medium from the holes under dark conditions.

Add serum-free culture medium containing the photosensitizer protoporphyrin chlorin (Ce6) into the holes and culture the cells under dark conditions.

Remove the culture medium from the holes under dark conditions.

Add fresh complete culture medium containing a ferroptosis inducer into the holes.

Use the light generated by the wireless self-powered photodynamic tablet, under ultrasound excitation (e.g., place the present photodynamic tablet in the holes and irradiate it with ultrasound radiation), to irradiate the fresh complete culture medium.

By following these steps, an anti-tumor model based on the wireless self-powered photodynamic tablet is obtained. This model incorporates tumor cells grown in the cell culture device, utilizes the photosensitizer Ce6 in a serum-free culture medium, introduces a ferroptosis inducer in fresh complete culture medium, and applies light emitted by the tablet under ultrasound excitation to facilitate the desired anti-tumor effects.

The present invention offers a significant benefit through its method for constructing an anti-tumor model based on the wireless self-powered photodynamic tablet. This method enables the implementation of complementary and synergistic anti-tumor treatment by combining PDT with a ferroptosis inducer. By replacing the photosensitizer, ferroptosis inducer, and culture medium, this innovative approach facilitates an optimized treatment strategy. Moreover, the present invention provides additional advantages that will be further examined in subsequent embodiments.

BRIEF DESCRIPTION OF THE DRAWINGS

To offer a more comprehensive understanding of the technical solutions presented in embodiments of the present invention, a concise introduction to the accompanying drawings utilized in the embodiments is provided below. It is important to note that these drawings solely represent specific embodiments of the invention and should not be regarded as restrictive to the scope. Those with ordinary skill in the relevant field can generate other relevant drawings based on these illustrations without significant creative effort.

The identified components in the above illustrations are as follows:

1. Wireless power supply unit; 2. Circuit unit; 201. Rectifier bridge; 202. Stabilizing capacitor; 3. Micrometer-scale LED array; 4. Flexible transparent biocompatible encapsulation; 5. Base; 6. Cell culture device; 7. Ultrasound probe; 8. Wireless self-powered optoacoustic tablet; 9. Ultrasound transmission gel layer; D1. First Schottky barrier diode; D2. Second Schottky barrier diode; D3. Third Schottky barrier diode; D4. Fourth Schottky barrier diode; LED1. First light-emitting diode; LED2. Second light-emitting diode.

DETAILED DESCRIPTION

The following section provides a comprehensive and precise description of the technical solutions presented in the embodiments of the present invention, in conjunction with the accompanying drawings. It is important to note that the described embodiments may constitute only a portion of the implementations of the present invention, rather than the entirety. Notably, the components described and depicted in the accompanying drawings can be arranged and designed in various configurations, and can include additional components. Therefore, the detailed description presented below, pertaining to the embodiments illustrated in the drawings, is not intended to impose limitations on the scope of the claimed invention. Instead, it serves as a representation of selected embodiments of the present invention. Additionally, it should be emphasized that, based on these embodiments, all other implementations that skilled individuals in the art can derive without significant creative effort fall within the scope of protection of the present invention.

Embodiment 1

Figure 1:
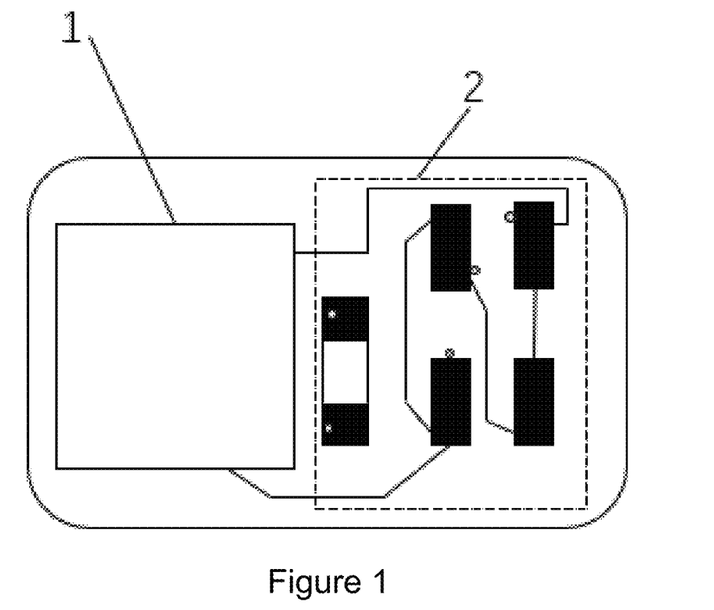
FIG. 1: The schematic diagram showcases one side of an unpackaged wireless self-powered optoacoustic tablet in embodiment 1 of the present invention.
Figure 2:
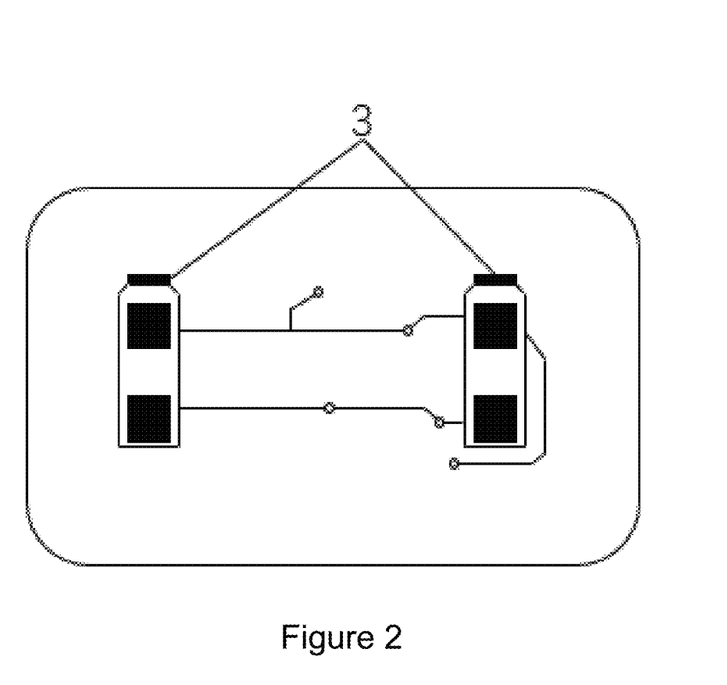
FIG. 2: This illustration presents another side of the unpackaged wireless self-powered optoacoustic tablet in embodiment 1 of the present invention.

In one embodiment of the present invention, as depicted in FIGS. 1 and 2, a wireless self-powered photodynamic tablet (referred to as tablet 8) is introduced. This tablet comprises several key components. Firstly, there is a wireless power supply unit (1) that is electrically connected to a circuit unit (2). Furthermore, the circuit unit (2) is connected to a micrometer-level LED array (3). To ensure protection and functionality, the wireless power supply unit (1), circuit unit (2), and micrometer-level LED array (3) are all encapsulated within a flexible transparent biocompatible enclosure (4).

The wireless self-powered photodynamic tablet (8) possesses specific dimensions, measuring 8 mm in length, 5 mm in width, and 3 mm in height. Additionally, it may have a weight of 0.44 g or thereabout.

The wireless power supply unit (1) is specifically designed to receive ultrasonic energy and efficiently convert it into electrical energy. It takes the form of a square plate-shaped piezoelectric ceramic made from lead zirconate titanate material. This ceramic component is electrically connected to both the circuit unit (2) and the micrometer-level LED array (3). With dimensions of 4 mm in length and width, and 1 mm in height, it ensures effective reception of ultrasonic energy from all directions and its subsequent conversion into electrical energy.

The circuit unit (2) plays a crucial role in rectifying the electrical energy generated by the wireless power supply unit (1) and ensuring stable transmission of the converted energy (e.g., electrical current) to the micrometer-level LED array (3).

Figure 3:
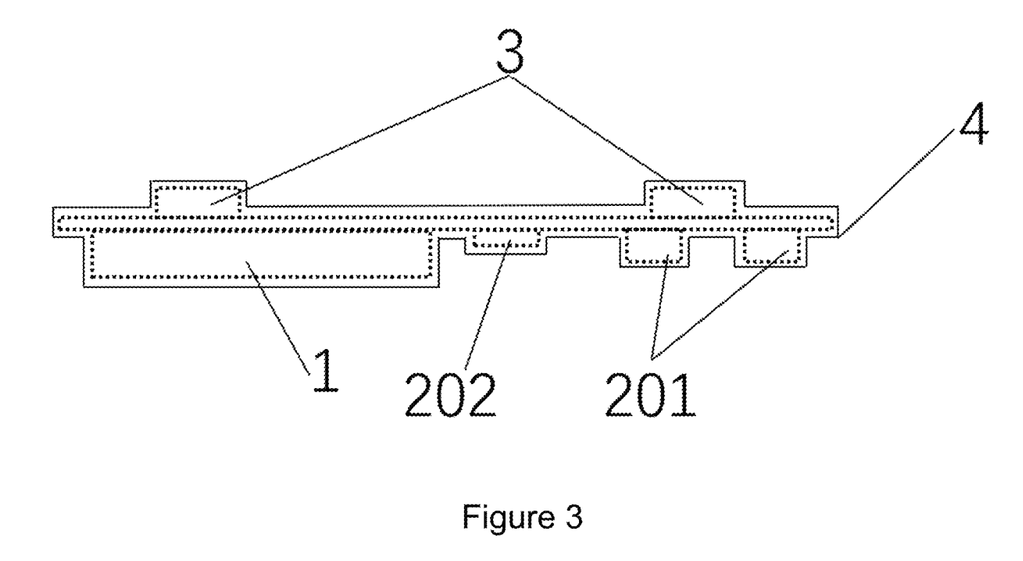
FIG. 3: The depicted diagram provides a side view of the packaged wireless self-powered optoacoustic tablet in embodiment 1 of the present invention.

FIGS. 1 and 3 illustrate the composition of the circuit unit (2), which includes of a rectifier bridge (201) and a voltage stabilizing capacitor (202) connected to the rectifier bridge (201).

Figure 4:
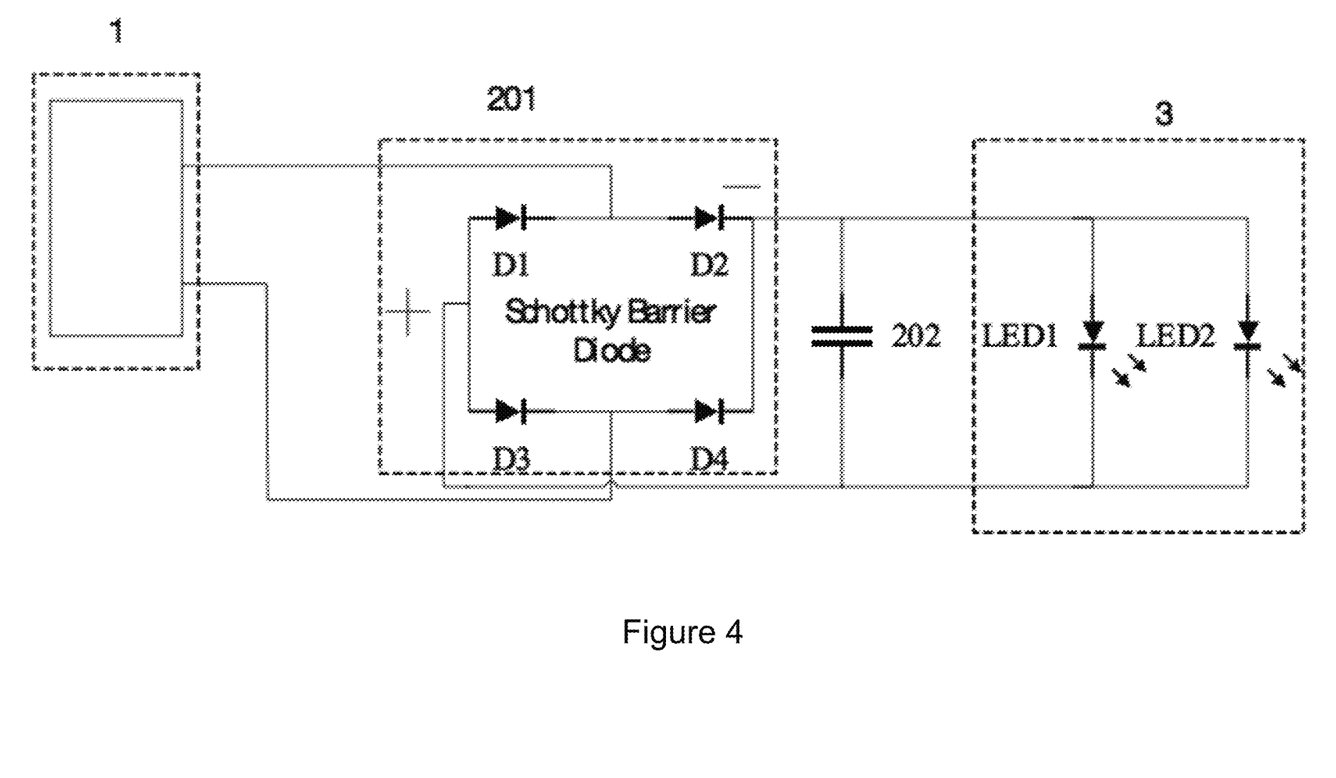
FIG. 4: The diagram illustrates the circuit principles of the wireless self-powered optoacoustic tablet in embodiment 1 of the present invention.

FIG. 4 illustrates the configuration of the rectifier bridge (201) in detail. The rectifier bridge (201) comprises four Schottky barrier diodes, namely D1, D2, D3, and D4.

The positive terminal of the first Schottky barrier diode, D1, serves as the positive terminal of the rectifier bridge (201). It is connected to the positive terminals of the third Schottky barrier diode, D3, one end of the voltage stabilizing capacitor (202), and the negative terminal of the micrometer-level LED array (3). On the other hand, the negative terminal of D1 is connected to the positive terminal of the second Schottky barrier diode, D2, as well as one end of the wireless power supply unit (1). The negative terminal of D2 acts as the negative terminal of the rectifier bridge (201). It is connected to the negative terminals of the fourth Schottky barrier diode, D4, the other end of the voltage stabilizing capacitor (202), and the positive terminal of the micrometer-level LED array (3). Moreover, the negative terminal of D3 is linked to the positive terminal of D4 and the other end of the wireless power supply unit (1). The rectifier bridge (201) plays a crucial role in converting the alternating current (AC) generated by the wireless power supply unit (1) into direct current (DC). This rectified DC is then stabilized by the voltage stabilizing capacitor (202) before being transmitted to the micrometer-level LED array (3).

Overall, this configuration ensures the efficient rectification and stabilization of the electrical energy for proper operation of the micrometer-level LED array (3). The micrometer-level LED array 3 receives the DC power and emits light of a specific wavelength to promote the production of lipid peroxides in tumor cells. It works in conjunction with an iron-based death inducer to induce ferroptosis in tumor cells. The LEDs in the micrometer-level LED array 3 have a length of 1 mm and width and height of 0.5 mm. In this embodiment, the ultrasonic energy can simultaneously activate two parallel micrometer-level LEDs, namely LED1 and LED2, to emit light having a wavelength of 660 nm, as light sources for the PDT light transmission.

The preparation method for the wireless self-powered photodynamic tablet (tablet 8) in this particular embodiment involves the following steps:

Pre-cleaning the wireless power supply unit (1) with ethanol and deionized water (in either sequence or together), followed by drying it in an oven.

As shown in FIGS. 1 and 2, soldering the wireless power supply unit (1) and the circuit unit (2) to one side of the circuit board, ensuring proper electrical connection between them. The wireless power supply unit (1) is constructed from a material capable of converting ultrasonic energy into electrical energy. Specifically, a square plate-shaped piezoelectric ceramic comprising lead zirconate titanate is utilized as the wireless power supply unit (1).

Soldering the micrometer-level LED array (3) to the other side of the circuit board, ensuring electrical connection between the circuit unit (2) and the micrometer-level LED array (3). The circuit board thus includes pass-through electrical connectors in locations where the electrical connections between the circuit unit (2) and the LED array (3) are to be made.

Encapsulating the soldered wireless power supply unit (1), circuit unit (2), and micrometer-level LED array (3) within a flexible, transparent, biocompatible enclosure (4), and allowing it to dry.

In this embodiment, a liquid mixture of polydimethylsiloxane (PDMS) and a conventional cross-linking agent in a mass ratio of 10:1 is treated in a vacuum environment for 5 minutes to remove any bubbles. Subsequently, the wireless self-powered photodynamic tablet (8) is encapsulated with the PDMS mixture and dried (e.g., the PDMS mixture is allowed to solidify).

Embodiment 2

Figure 5:
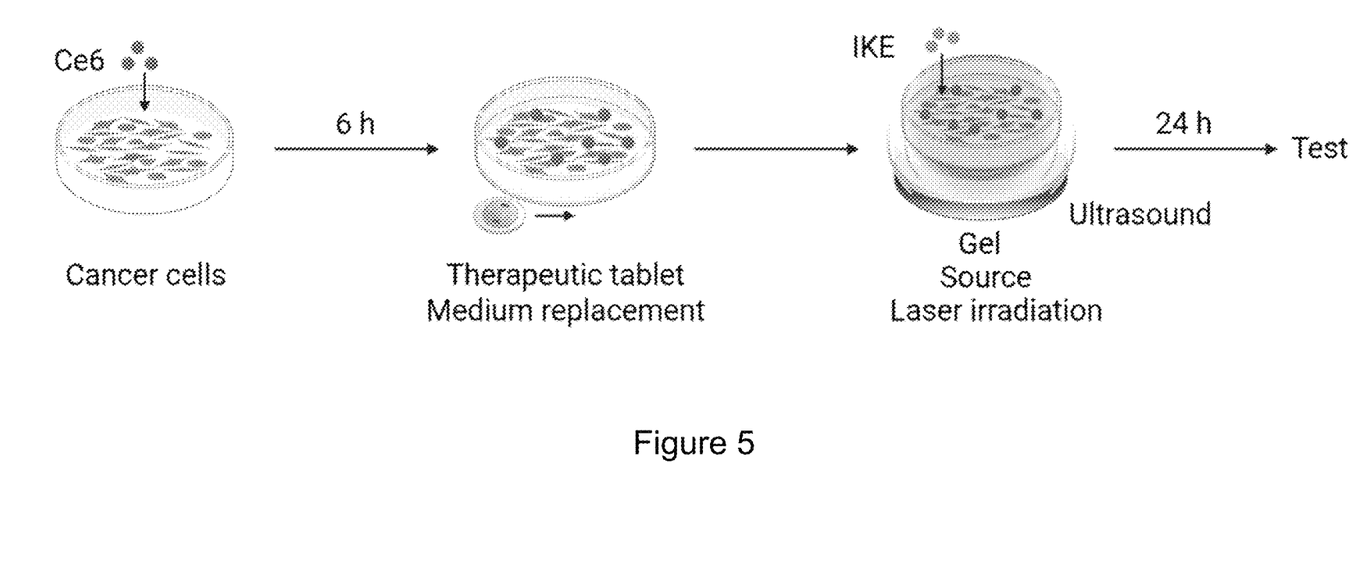
FIG. 5: The diagram depicts a schematic representation of an anti-tumor model based on the wireless self-powered optoacoustic tablet in embodiment 2 of the present invention.

In this embodiment, a method for constructing an anti-tumor model using the wireless self-powered photodynamic tablet (tablet 8) is presented, as depicted in FIG. 5. The system for constructing the anti-tumor model involves the following steps:

Inoculate a specific quantity of tumor cells into the wells of a cell culture device (6). Allow the cells to adhere and grow on the walls of the wells.

Remove the culture medium from the wells under dark conditions.

Add serum-free culture medium containing the photosensitizer Ce6 to the wells. Ensure that this step is carried out under dark conditions to avoid premature activation of the photosensitizer. Allow the cells to be cultured with the photosensitizer for a period of 6 hours.

After 6 hours of cultivation, remove the serum-free culture medium containing the photosensitizer Ce6 from the wells under dark conditions.

Add fresh complete culture medium containing a ferroptosis inducer and the wireless self-powered photodynamic tablet (8) to the wells. Use the light generated by the wireless self-powered photodynamic tablet (8) under ultrasound stimulation to irradiate the cells for 20 minutes, thus obtaining an anti-tumor model based on the wireless self-powered photodynamic tablet (8).

PDT is subject to the influence of the tumor's hypoxic microenvironment and treatment depth. The ferroptosis inducer, upon causing cell death, triggers the accumulation of divalent iron ions within the cells. This, in turn, stimulates the production of oxygen through the Fenton reaction, thereby ameliorating the hypoxic microenvironment of the tumor and facilitating sufficient oxygen supplementation for effective photodynamic therapy.

Figure 6:
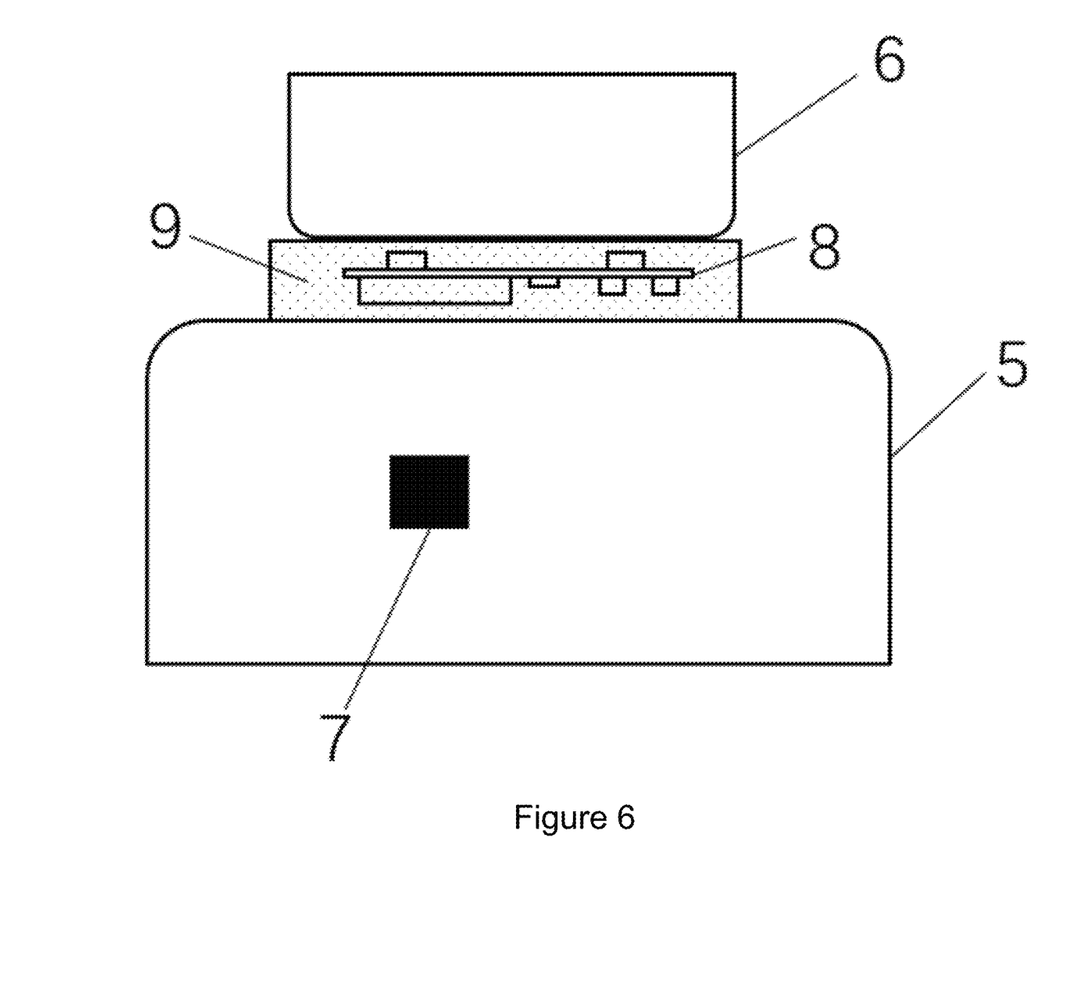
FIG. 6: The presented diagram illustrates a schematic representation of the system used to construct the anti-tumor model in embodiment 2 of the present invention.

FIG. 6 shows an implementation of the method for constructing the anti-tumor model utilizing the wireless self-powered photodynamic tablet (8), as described in this embodiment. This method is executed through a system comprising several components. The system comprises a base (5) and a cell culture device (6) thereover. Additionally, an ultrasound probe (7) that is externally connected to the base (5) is configured to emit ultrasound waves (radiation). Furthermore, the system incorporates the wireless self-powered photodynamic tablet (8) which emits light having a specific wavelength towards the cell culture device (6). This emission of light facilitates the production of lipid peroxides in the tumor cells and induces iron-induced cell death, in conjunction with the ferroptosis inducer.

The system employed for constructing the anti-tumor model is designed according to a treatment system that utilizes the wireless self-powered photodynamic tablet (8). This treatment system comprises two primary components: the wireless self-powered photodynamic tablet (8) itself and an ultrasound probe (7) configured to emit ultrasound waves towards the tablet. By integrating these components, the system facilitates the construction of the anti-tumor model by enabling targeted light application, activation of specific cellular processes, and induction of tumor cell death. The wireless self-powered photodynamic tablet (8) serves as the core element of the system, while the ultrasound probe (7) complements its functionality by providing ultrasound wave emission to the tablet.

When the ultrasound probe (7) is activated, it emits ultrasound waves at a frequency of 500 kHz. These ultrasound waves reach the implanted site of the wireless self-powered photodynamic tablet (8). At this location, the wireless power supply unit (1), constructed using a piezoelectric ceramic (specifically, lead zirconate titanate) with a piezoelectric effect, receives the ultrasound waves. As the ultrasound waves interact with the piezoelectric ceramic material, they cause slight deformations on its surface. This mechanical energy resulting from the ultrasound waves is then converted into electrical energy through the piezoelectric effect. The wireless power supply unit (1) outputs an alternating current (AC) through conductors. The AC output from the wireless power supply unit 1 passes through a rectifier bridge (201), which comprises a plurality of Schottky barrier diodes. In conjunction with a voltage-stabilizing capacitor (202), the AC current is rectified, resulting in the formation of stable direct current (DC). This stable DC current is then supplied to the micrometer-level LED array (3). Within the micrometer-level LED array (3), the first light-emitting diode (LED1) and the second light-emitting diode (LED2) are excited by the direct current. Consequently, these LEDs emit red light with a wavelength of 660 nm. This red light emission is specifically utilized for the purpose of PDT, contributing to the overall therapeutic process.

In this exemplary embodiment, a medical ultrasound gel layer (9) (ultrasound coupling agent) is between the cell culture device (6) and the upper surface of the base (5). This gel layer serves the purpose of minimizing acoustic impedance mismatch, thereby facilitating the efficient operation of the wireless self-powered photodynamic tablet (8) and ensuring optimal red light irradiation onto the tumor cells.

The cell culture device (6) is crafted from a transparent material and takes the form of a porous plate. Within this structure, the wireless self-powered photodynamic tablet (8) is situated within the medical ultrasound gel layer (9). The porous plate design allows for the concurrent cultivation of multiple tumor cell suspensions. By utilizing the same ultrasound source and employing irradiation from the wireless self-powered photodynamic tablet (8), it becomes feasible to establish multiple comparable anti-tumor models based on this technology. This enables convenient comparative analysis for further evaluation and assessment.

This embodiment provides a comprehensive account of constructing an anti-tumor model utilizing the wireless self-powered photodynamic tablet (8), using human lung cancer cells A549 and H1299, as well as mouse lung cancer cells LLC. The experimental procedure involved seeding 8,000 cells per well in a 96-well plate and allowing them to adhere for 24 hours. The cells were divided into four groups: control group (Ctrl), ferroptosis inducer (IKE) group, photodynamic therapy (PDT) group, and combined treatment of IKE and PDT (IKE+PDT) group. The culture medium was then replaced accordingly: the PDT and IKE+PDT groups received 100 μL of serum-free medium containing 8 μM photosensitizer Ce6, while the Ctrl and IKE groups were replaced with serum-free medium. Following this, the cells were incubated for 6 hours under light avoidance conditions (i.e., in the substantial absence of visible light). Subsequently, the culture medium was replaced again: the IKE and IKE+PDT groups received fresh complete medium containing 10 μM IKE, while the Ctrl and PDT groups received complete medium. The PDT and IKE+PDT groups underwent 20 minutes of photodynamic therapy (e.g., with 660 nm light from the photodynamic tablet). After 24 hours of incubation, a cell viability assay was conducted using the CCK-8 reagent kit. Each experiment was repeated three times, and the data were subjected to statistical analysis. The results demonstrated that the use of ferroptosis inducer alone resulted in a moderate decrease in cell viability compared to the control group, with reductions of 22.4%, 26.0%, and 30.3% in the three cell lines, respectively. However, the combined treatment of ferroptosis inducer and photodynamic therapy exhibited a significant decrease in cell viability compared to the control group. Specifically, reductions of 83.2%, 91.0%, and 91.1% were observed in the three cell lines, respectively, highlighting the enhanced anti-tumor efficacy of the combined treatment approach.

The aforementioned description merely represents specific embodiments of the invention, and it is important to note that the scope of the invention is not restricted solely to these embodiments. The invention can be applied to various cancer types, not limited to lung cancer, and the iron-induced cell death inducer mentioned in this embodiment, namely IKE, is just one example among many. Skilled individuals in the relevant field can readily conceive of alternative variations or substitutions within the technical framework disclosed in the present invention. It is imperative to encompass all such variations and substitutions within the scope of the invention, as they fall within the purview of a person skilled in the art.

What is claimed is:

1. A wireless self-powered photodynamic tablet, comprising a wireless power supply unit, an electrically connected circuit unit to the wireless power supply unit, a micrometer-scale LED array electrically connected to the circuit unit, and a flexible, transparent, biocompatible encapsulation that envelops the wireless power supply unit, the circuit unit, and the micrometer-scale LED array; wherein the circuit unit comprises a rectifier bridge and a voltage-stabilizing capacitor connected to the rectifier bridge;

the rectifier bridge includes a first Schottky barrier diode, a second Schottky barrier diode, a third Schottky barrier diode, and a fourth Schottky barrier diode;

the first Schottky barrier diode includes an anode the serves as a positive pole of the rectifier bridge, and is connected to a positive pole of the third Schottky barrier diode, one end of the voltage-stabilizing capacitor, and a negative pole of the micrometer-scale LED array;

the first Schottky barrier diode has a negative pole that is connected to a positive pole of the second Schottky barrier diode and one end of the wireless power supply unit;

the second Schottky barrier diode has a negative pole that serves as a negative pole of the rectifier bridge, and is connected to a negative pole of the fourth Schottky barrier diode, another end of the voltage-stabilizing capacitor, and a positive pole of the micrometer-scale LED array;

the third Schottky barrier diode has a negative pole that is connected to a positive pole of the fourth Schottky barrier diode and another end of the wireless power supply unit;

the rectifier bridge is configured to rectify an alternating current from the wireless power supply unit into direct current;

the voltage-stabilizing capacitor transmits the direct current to the micrometer-scale LED array;

the wireless power supply unit and the circuit unit are soldered to one side of a circuit board, and the wireless power supply is electrically connected to the circuit unit;

the micrometer-scale LED array is soldered to another side of the circuit board, and the circuit unit is electrically connected to the micrometer-scale LED array;

the wireless power supply unit is configured to receive ultrasonic energy and convert the ultrasonic energy into electrical energy;

the circuit unit is configured to rectify the electrical energy into direct current and transmit the direct current to the micrometer-scale LED array;

the micrometer-scale LED array is configured to receive the direct current and emit light of a set wavelength;

the wireless power supply unit comprises a square plate-shaped piezoelectric ceramic comprising lead zirconate titanate;

the wireless self-powered photodynamic tablet has a length of 8 mm, a width of 5 mm, and a height of 3 mm;

the wireless self-powered photodynamic tablet has a weight of 0.44 g;

the square plate-shaped piezoelectric ceramic has a length and a width of 4 mm and a height of 1 mm;

the LED(s) in the micrometer-scale LED array have a length of 1 mm and a width and a height of 0.5 mm.

2. A method for preparing the wireless self-powered photodynamic tablet as claimed in claim 1, including the following steps:

pre-cleaning the wireless power supply unit with ethanol and deionized water, and drying it in an oven;

soldering the wireless power supply unit and the circuit unit to the one side of the circuit board, and electrically connecting the wireless power supply unit to the circuit unit;

soldering the micrometer-scale LED array to the other side of the circuit board, and electrically connecting the circuit unit to the micrometer-scale LED array; and sealing the soldered wireless power supply unit, circuit unit, and micrometer-scale LED array with a flexible, transparent, biocompatible encapsulation and allowing the encapsulation to air dry.

3. A method for constructing an anti-tumor model based on a wireless self-powered photodynamic tablet, including the following steps:

inoculating a specific number of tumor cells into wells of a cell culture device;

allowing the cells to adhere and grow in a culture medium according to a standard cell culture protocol;

removing the culture medium from the wells under light-protected conditions;

adding a serum-free culture medium containing the photosensitizer Chlorin e6 (Ce6) to the wells and cultivating under light-protected conditions;

removing the serum-free culture medium from the wells under light-protected conditions; and adding fresh complete culture medium containing a ferroptosis inducer to the wells, and irradiating the fresh complete culture medium with light under ultrasonic excitation by the wireless self-powered photodynamic tablet as described in claim 1.

4. A system for constructing an anti-tumor model, comprising a base, a cell culture device on or over the base, an ultrasonic probe configured to emit ultrasonic waves that is externally connected to the base, and the wireless self-powered photodynamic tablet as described in claim 1, configured to emit the light of the set wavelength to the cell culture device.

5. The system according to claim 4, further comprising a medical ultrasound gel layer between the cell culture device and the base.

6. The system according to claim 5, wherein the cell culture device comprises a transparent material and a multi-well plate; and the wireless self-powered photodynamic tablet is in the medical ultrasound gel layer.

* * * * *